United States Patent
Cropper et al.

(10) Patent No.: US 9,913,790 B2
(45) Date of Patent: Mar. 13, 2018

(54) ANTIPERSPIRANT EMULSION STICKS

(71) Applicant: Conopco, Inc., Englewood Cliffs, NJ (US)

(72) Inventors: Martin Peter Cropper, Birkenhead (GB); Kevin Ronald Franklin, Wirral (GB)

(73) Assignee: Conopco, Inc., Englewood Cliffs, NJ (US)

( * ) Notice: Subject to any disclaimer, the term of this patent is extended or adjusted under 35 U.S.C. 154(b) by 0 days.

(21) Appl. No.: 15/029,286

(22) PCT Filed: Oct. 25, 2013

(86) PCT No.: PCT/EP2013/072420
§ 371 (c)(1),
(2) Date: Apr. 14, 2016

(87) PCT Pub. No.: WO2015/058812
PCT Pub. Date: Apr. 30, 2015

(65) Prior Publication Data
US 2016/0220463 A1    Aug. 4, 2016

(51) Int. Cl.
| | | |
|---|---|---|
| *A61K 8/42* | (2006.01) | |
| *A61K 8/34* | (2006.01) | |
| *A61K 8/37* | (2006.01) | |
| *A61K 8/44* | (2006.01) | |
| *A61K 8/02* | (2006.01) | |
| *A61K 8/06* | (2006.01) | |
| *A61K 8/28* | (2006.01) | |
| *A61K 8/41* | (2006.01) | |
| *A61K 8/894* | (2006.01) | |
| *A61Q 15/00* | (2006.01) | |

(52) U.S. Cl.
CPC .............. *A61K 8/42* (2013.01); *A61K 8/0229* (2013.01); *A61K 8/064* (2013.01); *A61K 8/28* (2013.01); *A61K 8/342* (2013.01); *A61K 8/37* (2013.01); *A61K 8/41* (2013.01); *A61K 8/442* (2013.01); *A61K 8/894* (2013.01); *A61Q 15/00* (2013.01); *A61K 2800/262* (2013.01); *A61K 2800/34* (2013.01)

(58) Field of Classification Search
CPC . A61K 8/42; A61K 8/342; A61K 8/37; A61K 8/442; A61K 8/0229; A61K 8/064; A61K 8/28; A61K 8/41; A61K 8/894; A61K 2800/262; A61K 2800/34; A61Q 15/00
See application file for complete search history.

(56) References Cited

U.S. PATENT DOCUMENTS

| | | | |
|---|---|---|---|
| 6,241,976 B1 | 6/2001 | Esser | |
| 6,652,843 B2 | 11/2003 | Fairclough | |
| 7,347,990 B2 | 3/2008 | Emslie | |
| 7,347,992 B2 | 3/2008 | Franklin | |
| 2002/0039563 A1 | 4/2002 | Franklin et al. | |
| 2004/0223994 A1* | 11/2004 | Emslie | A61K 8/0229 424/401 |
| 2004/0223996 A1 | 11/2004 | Franklin | |

FOREIGN PATENT DOCUMENTS

| | | |
|---|---|---|
| EP | 2181691 | 5/2010 |
| EP | 3060193 | 7/2017 |
| WO | WO0061094 | 10/2000 |
| WO | WO03059307 A1 | 7/2003 |
| WO | WO03059308 | 7/2003 |

OTHER PUBLICATIONS

GB Search Report in GB1318882 dated Dec. 18, 2013.
Search Report & Written Opinion in PCTEP2013072420 dated Jul. 24, 2014, pp. 1-3.

* cited by examiner

*Primary Examiner* — Ali Soroush
(74) *Attorney, Agent, or Firm* — Karen E. Klumas

(57) ABSTRACT

The invention relates to a water-in-oil antiperspirant composition comprising: A) an aqueous phase containing dissolved antiperspirant active; B) an oil phase comprising: i) an amido gelator; ii) a fatty alcohol that is liquid at 25° C.; iii) a primary non-volatile emollient oil having a refractive index of from 1.47 to 1.56; iv) a secondary non-volatile emollient oil having a refractive index of from 1.38 to 1.451 and C) and emulsifier; and further to a method of production of said antiperspirant composition.

14 Claims, No Drawings

ANTIPERSPIRANT EMULSION STICKS

BACKGROUND OF THE INVENTION

Antiperspirant emulsion sticks are solidified compositions characterized as having aqueous and oil phases. Among such antiperspirant emulsion sticks are compositions having a disperse aqueous phase in which is dissolved antiperspirant active, commonly aluminium, zirconium and/or mixed aluminium/zirconium salts, and a continuous oil phase comprising one or more gelling agents capable of structuring such phase.

Antiperspirant emulsion sticks can be formulated as clear (i.e., translucent or transparent) or opaque compositions. Translucent or transparent emulsion sticks go on clear and, depending upon their formulation, may remain clear for extended periods of time, reducing the consumer perceived negative of "white marks" associated with deposition of antiperspirant active.

In antiperspirant emulsion sticks, clarity of the stick itself is commonly achieved through a combination of technology approaches. Solidifying the emulsion with a structurant that has a very fine and homogeneous microstructure provides a stick in which light scattering is minimized. Emulsion sticks in which the oil phase is structured with a fiber-forming amido gelator and a liquid fatty alcohol represent a class of sticks having relatively fine and homogeneous microstructures. Such emulsion sticks are described, for example, in U.S. Pat. Nos. 6,241,976 and 7,347,990. The extent to which an emulsion's aqueous and oil phases are matched is another factor that impacts stick clarity.

On a production scale, there are a number of significant challenges to achieving RI matching of the aqueous and oil phases, including lot-to lot variability in the refractive indices of raw materials, principally the antiperspirant active. As a practical matter, adjusting the emulsion to a fixed RI for all batches is not trivial and tends to be done by trial and error. While the refractive index of the aqueous phase varies with active concentration, the variation typically does not follow a linear progression. Moreover, to achieve optimum sensory properties, the water content in proportion to active is relatively fixed, i.e., water is typically present in an amount sufficient for the active to be dissolved without giving rise to a formulation that is "wet" or "sticky". Accordingly, it is generally more desirable to modify the oil phase to match the refractive index of the aqueous phase, rather than modifying the refractive index of the aqueous phase to match that of the oil phase.

While the oil phase offers more flexibility in terms of refractive index matching, it too has constraints, one such constraint being the need to solubilize the gelator (herein also referred to as the gelling agent or gellant) during stick preparation. Liquid fatty alcohols such as, for example, isostearyl alcohol and octyl dodecanol are known to be especially effective in solubilizing amido gelators. While desirable for their solubility properties, owing to their heavy, oily feel, liquid fatty alcohols tend to detract from sensory properties. To optimize sensory properties, it is generally desirable to minimize the amount of liquid fatty alcohol, and to further include in the oil phase a relatively high level of oil with better sensory properties. Typically such oil includes volatile oil, in particular, volatile silicone oil.

The volatile silicone oil of choice is commonly cyclomethicone. Cyclomethicone is nominally designated as D4, D5 or D6, depending upon the particular cyclomethicone (e.g., cyclotetrasiloxane, cyclopentasiloxane or cyclohexasiloxane) predominant therein. Cyclomethicone is compatible with numerous carrier oils as well as with amido gelators and emulsifiers, in particular, the silicone based emulsifiers commonly employed in such compositions. Volatile silicone oils are generally considered to impart good sensory feel to such formulations, i.e., a clean, dry feel. Additionally, the surface tension and spreadability of cyclomethicone can contribute to the emulsion sticks in which they are used having a smooth or silky feel on application.

Volatile linear polydimethylsiloxanes, often referred to as volatile dimethicones, such as, for example, those sold by Dow Corning with the names DC200 Fluid 1 cst and DC200 Fluid 5 cst, are in some cases used as complete or partial alternatives to the cyclomethicones. Non-silicone volatile oils may also be employed for similar sensory purposes. These include linear and branched hydrocarbons containing less than about 16 carbon atoms.

Volatile oil may, however, evaporate during stick production thereby contributing to mismatching of the refractive index of the oil and aqueous phases which, in turn, can lead to stick clarity being compromised. In addition to volatile oil potentially contributing to RI mismatch, its use may complicate emulsion stick production, particularly if the processing temperature of the amido gelator exceeds the flash point of the volatile oil.

As well as offering potential processing advantages, minimizing volatile oil content may be desirable from an environmental or regulatory perspective.

It is an aspect of the present invention to provide an antiperspirant emulsion stick that overcomes or ameliorates one or more of the issues disclosed above. More particularly, one aspect of this invention is to provide an emulsion stick that includes an amido gelator and a solvent fatty alcohol, in which composition the RI of the aqueous and oil phases are relatively easily matched. Another aspect of this invention is to minimize or virtually eliminate volatile silicone oil and other volatile oils (exclusive of perfume oil), while providing a stick that retains desirable clarity and sensory feel. In one or more embodiments, another aspect of this invention is to virtually eliminate silicone oil in an antiperspirant emulsion stick while retaining the ability to use a silicone based emulsifier therein.

SUMMARY OF THE INVENTION

It has been found that in an emulsion antiperspirant stick comprising an amido gelator and a liquid fatty alcohol by employing, in addition to the liquid fatty alcohol, a combination of high and low refractive index (RI) non-volatile, emollient oils, the RI of the oil phase can be readily adjusted to match that of the aqueous phase. By adjusting the relative amounts of the high RI (e.g. RI of from 1.47 to 1.56) and low RI (e.g. RI of from 1.38 to 1.45) oils, it is possible to adjust the refractive index of the oil phase over a significant and suitable RI range. Moreover, as the RI of the oil phase commonly varies in what is generally a relatively linear way, weight averaging or, more preferably, volume averaging the RIs of the individual emollient oils and liquid fatty alcohol affords formulators a predictable means of making refractive index adjustments.

It has further been found that through the use of a particular combination of non-volatile emollient oils, liquid fatty alcohol and gelling agent, it is possible to reduce or virtually eliminate volatile silicone oil and, in one or more embodiments, volatile oil in general (exclusive of perfume oil), while providing antiperspirant emulsion stick compositions that afford desirable sensory properties when applied to the underarm.

In one embodiment of this invention there is provided a emulsion antiperspirant composition comprising:
A) an aqueous phase containing dissolved antiperspirant active
B) an oil phase comprising:
  i) at least one amido gelator;
  ii) at least one fatty alcohol that is liquid at 25° C.;
  iii) at least one primary non-volatile emollient oil having a refractive index (RI) that is from 1.47 to 1.56;
  iv) at least one secondary non-volatile emollient oil having an RI that is from 1.38 to 1.45; and
C) an emulsifier,
wherein:
  a) the stick is at least translucent in appearance; and
  b) the primary and secondary emollient oils combined account for from 5 to 65% by weight the oil phase;
  c) the composition is in the form of a solid stick;
  d) the composition contains from 0 to 0.5 wt. %, preferably from 0 to 0.1 wt. % of volatile oil, exclusive of perfume oil;
  e) the ratio, by weight, of the combination of primary non-volatile, emollient oil and secondary non-volatile emollient oil to fatty alcohol is from 2:1 to 1:20;
  f) the ratio, by weight of primary non-volatile emollient oil to secondary non-volatile emollient oil is from 1:20 to 20:1;
  g) the ratio, by weight, of fatty alcohol to amido gelator is from 2:1 to 6:1, preferably from 3:1 to 5:1; and,
  h) if present, the composition contains at most 2.5 wt. %, preferably at most 2 wt. %, more preferably at most 1.5 wt. % of non-volatile aliphatic dimethicone oil.

Preferably the composition has a % Light Transmission Value greater than 5%.

Preferably the amido gelator comprises at least one N-acyl amino acid amide.

Preferably the composition is free of volatile silicone oil, exclusive of perfume oil.

Preferably the composition further comprises perfume oil and/or glycine.

Preferably the amido gelator comprises N-lauryl-L-glutamic acid, di-n-butyl amide and N-ethyl hexanoyl-L-glutamic acid, di-n-butylamide.

Preferably the RI of the aqueous and oil phases are matched to within 0.002 units.

Preferably the composition comprises from 4 to 12% by weight, based on the total weight, based on the total weight thereof of a combination of amido gelators of the formula $N^x$—CO—$R^x$ and $A^y$-CO—$R^y$ wherein $R^x$ represents a branched alkyl group containing from 4 to 12 carbon atoms, $R^Y$ represents a linear alkyl group containing from 9 to 21 carbon atoms and $A^x$ and $A^Y$ independently represent an amino acid amide residue.

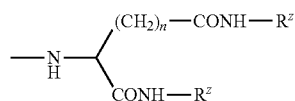

in which n represents an integer of 1 or 2 and $R^Z$ represents an alkyl group, which can be linear or branched, containing from 1 to 10, which $R^Z$ groups can be the same or different.

Preferably the emulsifier comprises polyoxyalkylene modified dimethylpolysiloxane.

Preferably the fatty alcohol comprises isostearyl alcohol.

Preferably the amido gelator comprises at least 90% by weight of all gelling agent present in the composition.

Preferably the total amount of wax, if present, does not exceed 1% by weight, based on the total weight of the composition.

Preferably the secondary non-volatile oil is selected from the group consisting of dioctyl ether, dioctyl carbonate, isopropyl palmitate, isopropyl myristate, PPG-4 butyl ether, or a mixture thereof.

In a second aspect, the invention is directed to methods for preparing such antiperspirant compositions.

DETAILED DESCRIPTION OF THE INVENTION

Except in the operating and comparative examples, or where otherwise explicitly indicated, all numbers in this description indicating amounts, parts, percentages, ratios, and proportions of material, physical properties of material, and conditions of reaction are to be understood as modified by the word "about". All parts, percentages, ratios, and proportions of material referred to in this description are by weight unless otherwise indicated.

The term "comprising" is meant not to be limiting to any subsequently stated elements but rather to encompass non-specified elements of major or minor functional importance. In other words, the listed steps, elements or options need not be exhaustive. Whenever the words "including" or "having" are used, these terms are meant to be equivalent to "comprising" as defined above. Where the compositions of the subject invention are described as "including" or "comprising" specific components or materials, narrower embodiments where the compositions can "consist essentially of" or "consist of" the recited components or materials are also contemplated.

It should also be noted that in specifying any range of concentration or amount, any particular upper concentration or amount can be associated with any particular lower concentration or amount.

As used herein the term "non-volatile" is used to designate a material having a vapor pressure of below 1 Pa at 25° C. (and for many non-volatile materials is less than 0.1 Pa.), whereas, the term "volatile" is used to designate a material having a vapor pressure at 25° C. that is at least 1 Pa.

As used herein, "clear" in reference to refers to the compositions of the subject invention means that the solidified compositions are "transparent" or "translucent". The term "transparent" as used in the subject specification and claims is intended to connote its usual diction definition. Thus, a transparent emulsion stick, like glass, allows for ready viewing of objects behind it. By contrast, a translucent emulsion stick, although allowing light to pass through the stick, causes the light to be scattered so that objects behind the translucent stick, while visible, are less clearly identified. The subject compositions are "clear" in the sense of the solidified compositions being at least translucent, with solidified compositions that are transparent being preferred in one or more embodiments.

The RI of the oil phase and the water phase are preferably matched. In the context of refractive index, by "matched" it is meant that the difference between the referenced refractive indices, as, for example, between the refractive index of matched oil and aqueous phases, is less than 0.005 units, preferably less than 0.002 units, at 25° C.

Except where otherwise indicated, in the description and claims all refractive index (RI) measurements are at 25° C.

RI is conveniently measured with a Bellingham & Stanley RFM 340 or similar refractometer. Other similar refractometers are also suitable.

Continuous Phase Gelator

The present invention is directed to water-in-oil emulsions in which a continuous oil phase, alternatively referred to as a water-immiscible phase, is solidified with one or more fiber-forming structurants known as N-acyl amido derivatives of amino acids, such fiber-forming structurants being herein alternatively referred to by the terms "N-acyl amino acid amides" or as "N-acyl amido derivatives of amino acids" or, more simply, as "amido", "N-acyl amino acid" or "amino acid amide" gelators, gelling agents, or gellants. Many N-acyl amido derivatives of amino acids suitable for solidifying cosmetically-acceptable oils have been described by Ajinomoto Co. Ltd. in U.S. Pat. No. 3,969,087 and U.S. Pat. Publn 2002/0159961. Other suitable amido gelators are described in U.S. Pat. No. 7,347,990, incorporated herein by reference.

The gelators suitable for use herein include N-acyl amino acid amides that satisfy the general formula:

$$A^x\text{—CO—}R^x \tag{1}$$

in which $A^x$ represents the residue of an amino acid amide and $R^x$ represents a branched alkyl group containing from 4 to 12 carbon atoms and sometimes 7 to 10 carbon atoms. In many instances, the amino acid amide residue $A^X$ can be represented by formula (2):

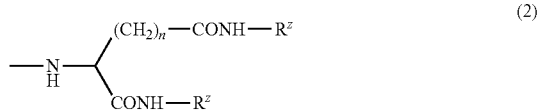

(2)

in which n represents an integer of 1 or 2 and $R^Z$ represents an alkyl group, which can be linear or branched, containing from 1 to 10 and, more particularly, from 3 to 5 carbon atoms, each of which $R^Z$ groups can be the same or different.

The amino acid from which such an amide residue $A^x$ is derivable is commonly glutamic or aspartic acid. In some especially preferred embodiments, each $R^Z$ represents a butyl group, especially an n-butyl group, and particularly in the derivative of glutamic acid, which residue is represented by formula (3)

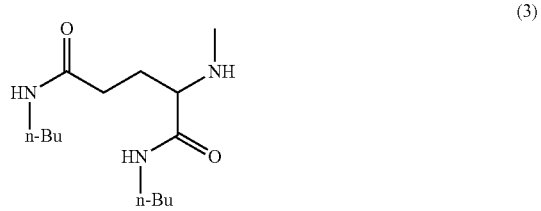

(3)

In formula (1), $R^X$ preferably represents an alkyl group containing one, two or possibly three side chains, with alkyl groups having one side chain being of particular interest in one or more embodiments. Desirably, any side chain in $R^x$ contains from 1 to 4 carbon atoms, such as methyl, ethyl propyl or butyl, and often from 1 to 3 carbon atoms, of which ethyl is very convenient. The alkyl backbone preferably contains from 4 to 8 carbon atoms and often from 4 to 7 carbon atoms. The location of the side chain along the alkyl group backbone is at the discretion of the producer, of which the 2 position is often favoured. An especially desirable branched chain group for $R^X$ is 1-ethylpentyl, so that the resultant acyl group is 2-ethylhexanoyl. Other branched chain groups for $R^X$ include 1-methylbutyl, isobutyl and 1-butylheptyl. Especially desirable are formula 1 gellants in which the amide residue is derived from glutamic acid dibutylamide. Among the formula 1 gellants of particular interest is N-ethylhexanoyl-L-glutamic acid, di-n-butylamide, which material is commercially available from Ajinomoto under the trade name EB21 or GA-01, Other N-acyl amino acid gelling agents suitable for use herein are satisfy the formula:

$$A^Y\text{—CO—}R^Y \tag{4}$$

in which $A^Y$ represents an amino acid amide and $R^Y$ represents a linear alkyl group containing from 9 to 21 carbon atoms. In one or more embodiments $A^Y$ desirably represents an amino acid amide residue in accordance with the formula (5)

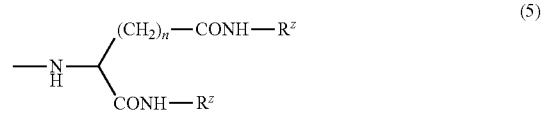

(5)

in which n represents an integer of 1 or 2 and $R^Z$ represents an alkyl group, which can be linear or branched, containing from 1 to 10 and particularly from 3 to 5 carbon atoms, which $R^Z$ groups can be the same or different. In one or more embodiments the amino acid from which such an amide residue $A^Y$ is derivable is desirably glutamic or aspartic acid. In some especially preferred embodiments, each $R^Z$ represents a butyl group, especially an n-butyl group, and particularly in the derivative of glutamic acid. Such a particularly preferred residue $A^Y$ is likewise represented by formula (3) given supra for residue $A^X$.

In formula (4), $R^Y$ often contains from 9 to 15 linear carbons, of which one preferred group comprises undecyl. N-Lauroyl-L-glutamic acid di-n-butylamide of the formula:

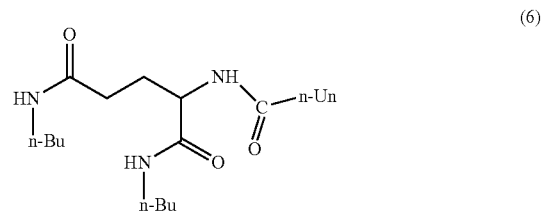

(6)

is an especially desirable amido gelator for employment in the instant invention compositions; such gelator is commercially available from Ajinomoto under the trade designation GP-1.

The proportion of amido gelator in the composition is generally determined in relation to the oil phase which it is structuring and the desired hardness of the stick. Commonly, the weight proportion of amido gelator in the subject composition is commonly selected in the range of 1 to 15 wt. %, more particularly, from 2 to 12 wt. % and, in some embodiments, from 3 to 10 wt. %, based on the total weight of the composition. When expressed in relation to the oil phase the amount of amido gelator is typically from 4 to 25 wt %, more particularly, from 8 to 22 wt. % by weight of the oil phase, In one or more embodiments of interest, in relation to the oil phase, the amount of amido gelator is from 10 to 17 wt % thereof.

Of particular interest are mixed gellant systems that include combinations of formula 1 and formula 4 N-acyl amino acid gelators. In such mixed gellant systems, the weight ratio of the formula 1 gellant to the formula gellant 4 is often selected in the range of from 3:1 to 1:3. In many instance the weight ratio is no higher than 2:1 and in such or other instances, the weight ratio is at least 1:2. A convenient weight ratio can be in the range of 1.1:1 to 1:1.1.

In one preferred embodiment of a mixed gellant system, the combined weight proportion of gellants 1 and 4 is the range of from 4 to 12% by weight and in some well desired embodiments from 5 to 9% by weight, based on the total weight of the composition.

Continuous Phase—Carrier Liquid

The carrier liquid for the oil or water-immiscible phase comprises a mixture of materials which are relatively hydrophobic so as to be immiscible in water. Following partition between the continuous oil phase and the disperse aqueous phase, a small fraction of hydrophilic liquid may remain in the continuous phase, provided the overall carrier liquid mixture is immiscible with water. It will generally be desired that the carrier mixture is liquid (in the absence of gelling agent) at temperatures of 15° C. and above.

The carrier liquid employed herein includes one or more liquid fatty alcohols. As referred to herein, "liquid fatty alcohols" are water-immiscible aliphatic alcohols having at least one alkyl chain of at least 10 carbon atoms, which alcohols are liquid at 20° C. and desirably have a boiling point of higher than 100° C. These include branched chain alcohols of at least 10 carbon atoms and in many instances up to 30 carbon atoms, particularly 15 to 25, such as isostearyl alcohol, hexyl-decanol and octyl-dodecanol. Other suitable water-immiscible aliphatic alcohols include intermediate chain length linear alcohols, commonly containing from 9 to 13 carbon atoms, such as decanol or dodecanol. Such alcohols can assist in the process of forming a solution of the amido-substituted gelators in the water-immiscible phase during the manufacture of structured gels. Such alcohols can often constitute from at least 10% by weight at least or 15% by weight of the oil phase, in many desirable mixtures comprising up to 70% or 80% by weight of the oil phase. In a number of convenient formulations, the proportion of such aliphatic alcohols in said mixture is from 10 or 15% to 30% by weight and in some others, the proportion is greater than 30% by weight.

Aliphatic alcohols which are solid at 20° C., e.g., long chain linear alcohols, such as stearyl alcohol are preferably absent or present in no more than 1% by weight, more particularly, no more than 0.5% by weight of the whole composition, since they lead to visible white deposits when a composition is topically applied to skin.

The oil phase further includes primary and secondary emollient oils. As used herein the term "emollient oil" refers to a water-immiscible, non-volatile oil that is liquid at 20° C., excluding oils that are liquid fatty alcohols. Preferably the emollient oil has a boiling point above 100° C., more preferably above 150° C.

Suitable emollient oils comprise liquid aliphatic or aromatic esters. Suitable aliphatic esters contain at least one long chain alkyl group, such as esters derived from $C_1$ to $C_{20}$ alkanols esterified with a $C_8$ to $C_{22}$ alkanoic acid or $C_6$ to $C_{10}$ alkanedioic acid. The alkanol and acid moieties or mixtures thereof are preferably selected such that they each have a melting point of below 20° C. These esters include isopropyl myristate, lauryl myristate, isopropyl palmitate, diisopropyl sebacate, diisopropyl adipate and triethylhexanoin.

Suitable liquid aromatic esters, preferably having a melting point of below 20° C., include fatty alkyl benzoates. Examples of such esters include suitable $C_8$ to $C_{18}$ alkyl benzoates or mixtures thereof, including in particular $C_{12}$ to $C_{15}$ alkyl benzoates e.g., those available under the trademark Finsolv$^{TN}$. An aryl benzoate, such as benzyl benzoate can also be used. Incorporation of such alkyl or aryl benzoate esters as at least a fraction of the hydrophobic carrier liquid can be advantageous.

Further instances of suitable emollient oils comprise liquid aliphatic ethers derived from at least one fatty alcohol, such as myristyl ether derivatives e.g. PPG-3 myristyl ether or lower alkyl ethers of polygylcols such as an ether having named as PPG-14 butyl ether by the CTFA.

Other soluble emollient oils include natural oils, including, for example, natural ester oils derived from glycerol and fatty acids containing at least 6 carbon atoms. Natural ester oils of particular interest for use herein comprise one or more unsaturated fatty acid glycerides. The fatty acid residues in the oils can comprise, commonly, from one to three olefinic unsaturated bonds and often one or two. While in many instances the olefinic bonds adopt the trans configuration, in a number of desirable products the bond or bonds adopt the cis configuration. If two or three olefinic unsaturated bonds are present, they can be conjugated. The fatty acid can also be substituted by a hydroxyl group. The natural oils employable herein desirably comprise one or more triglycerides of oleic acid, linoleic acid, linolenic acid or ricinoleic acid. Natural oils containing one or more of such triglycerides include coriander seed oil, impatiens balsimina seed oil, parinarium laurinarium kernel fat, sabastiana brasilinensis seed oil, dehydrated castor seed oil, borage seed oil, evening primrose oil, aquilegia vulagris oil, sunflower oil, olive oil, and safflower oil.

While selected non-volatile silicon-containing emollient oils, in particular, aryl methicones such as phenyl dimethicones and phenyl trimethicone, are suitable for use as the RI matching emollient oils, it is generally desirable that the compositions contain little or no non-volatile aliphatic dimethicone, i.e., from 0 to 2.5 wt % thereof, as these can phase separate from the full oil mixture leading to a heterogeneous oil phase and consequent loss of clarity.

Aqueous Disperse Phase

The emulsions herein contain an aqueous disperse phase in which is dissolved antiperspirant active. In addition to water, the aqueous disperse phase can comprise one or more water soluble or water miscible liquids. The proportion of water in the aqueous phase is often selected in the range of up to 70%, and particularly from 10% up to 50% or 60%.

One class of water soluble or water-miscible liquids comprises short chain monohydric alcohols, e.g. $C_1$ to $C_4$ and especially ethanol or isopropanol, which can impart a deodorizing capability to the formulation. Ethanol gives a cooling effect on application to skin, because it is very volatile. It is preferred that the content of ethanol or any other monohydric alcohol with a vapour pressure above 1.3 kPa (10 mmHg) is not over 15% better not over 8% by weight of the composition.

A further class of hydrophilic liquids comprises diols or polyols preferably having a melting point of below 40° C., or which are water miscible. Examples of water-soluble or water-miscible liquids with at least one free hydroxy group include ethylene glycol, 1,2-propylene glycol, 1,3-butylene glycol, hexylene glycols, such as, particularly, 1,2-hexane diol, diethylene glycol, dipropylene glycol, 2-ethoxyethanol, diethylene glycol monomethylether, triethyleneglycol monomethylether, glycerol, sorbitol, and water soluble polyalkylene glycol, such as, for example, water soluble polyethylene glycol, a non-limiting example of which is PEG 400 (aka PEG 8). Especially preferred are propylene glycol, glycerol and water soluble polyethylene glycol.

The aqueous phase of the emulsion can additionally comprise an amino acid such as glycine or histidine, for example in a concentration of up to 10% by weight of the composition, such as from 3 to 8% by weight.

In emulsions herein the disperse phase normally constitutes from 5 to 80 or 85% of the weight of the composition preferably from 5 to 50 or 65% and more preferably from 25 or 35% up to 50 or 65%, while the emulsifier and the continuous phase with the structurant system and any water-immiscible cosmetic actives therein provides the balance. The weight proportion of continuous phase normally constitutes from 15 or 35% up to 95% of the weight of the composition. Compositions with high proportion of disperse phase, i.e. from 65 to 85 wt. % disperse phase, may be advantageous because they can give good hardness even though the concentration of structurant may be only a small percentage of the total composition. However, compositions with a lower proportion of disperse phase can also be advantageous because they tend to offer a drier and warmer feel.

Antiperspirant Active

Antiperspirant actives, are preferably incorporated in an amount of from 0.5-60%, particularly from 5 to 30% or 40% and especially from 5 or 10% to 30 or 35% of the weight of the composition.

Antiperspirant actives for use herein are typically selected from astringent active salts, including in particular aluminum, zirconium and mixed aluminum/zirconium salts, including both inorganic salts, salts with organic anions and complexes. Preferred astringent salts include aluminum, zirconium and aluminum/zirconium halides and halohydrate salts, such as chlorohydrates and activated aluminum chlorohydrates.

Aluminum halohydrates are usually defined by the general formula $Al_2(OH)_xQ_y.wH_2O$ in which Q represents chlorine, bromine or iodine, x is variable from 2 to 5 and x+y=6 while $wH_2O$ represents a variable amount of hydration. Especially effective aluminum halohydrate salts, known as activated aluminum chlorohydrates, are described in EP-A-6739 (Unilever N V et al), the contents of which specification is incorporated herein by reference. Some activated salts do not retain their enhanced activity in the presence of water but are useful in substantially anhydrous formulations, i.e. formulations which do not contain a distinct aqueous phase.

Zirconium actives can usually be represented by the empirical general formula: $ZrO(OH)_{2n-nz}B_z.wH_2O$ in which z is a variable in the range of from 0.9 to 2.0 so that the value 2n−nz is zero or positive, n is the valency of B, and B is selected from the group consisting of chloride, other halide, sulphamate, sulphate and mixtures thereof. Possible hydration to a variable extent is represented by $wH_2O$. Preferable is that B represents chloride and the variable z lies in the range from 1.5 to 1.87. In practice, such zirconium salts are usually not employed by themselves, but as a component of a combined aluminum and zirconium-based antiperspirant.

The above aluminum and zirconium salts may have co-ordinated and/or bound water in various quantities and/or may be present as polymeric species, mixtures or complexes. In particular, zirconium hydroxy salts often represent a range of salts having various amounts of the hydroxy group. Zirconium aluminum chlorohydrate may be particularly preferred.

Antiperspirant complexes based on the above-mentioned astringent aluminum and/or zirconium salts can be employed. The complex often employs a compound with a carboxylate group, and advantageously this is an amino acid.

Examples of suitable amino acids include dl-tryptophan, dl-β-phenylalanine, dl-valine, dl-methionine and β-alanine, and preferably glycine which has the formula $CH_2(NH_2)COOH$.

It is highly desirable to employ complexes of a combination of aluminum halohydrates and zirconium chlorohydrates together with amino acids such as glycine, which are disclosed in U.S. Pat. No. 3,792,068 (Luedders et al). Certain of those Al/Zr complexes are commonly called ZAG in the literature. ZAG actives generally contain aluminum, zirconium and chloride with an Al/Zr ratio in a range from 2 to 10, especially 2 to 6, an Al/Cl ratio from 2.1 to 0.9 and a variable amount of glycine. Actives of this preferred type are available from SummitReheis and Guilini.

When the active antiperspirant salt is incorporated in solution in a hydrophilic solvent such as a glycol, its weight commonly excludes any water of hydration present.

The antiperspirant active will often provide from 3 to 60% by weight of the disperse phase, particularly from 10% or 20% up to 55% or 60% of that phase.

Emulsifier

The emulsion compositions herein will generally include one or more emulsifying surfactants which may be anionic, cationic, zwitterionic and/or nonionic surfactants. The proportion of emulsifier in the composition is often selected in the range up to 10% by weight and in many instances from 0.1 or 0.25 up to 5% by weight of the composition. Most preferred is an amount from 0.1 or 0.25 up to 3% by weight. Nonionic emulsifiers are frequently classified by HLB value. It is desirable to use an emulsifier or a mixture of emulsifiers with an overall HLB value in a range from 2 to 10 preferably from 3 to 8.

It may be convenient to use a combination of two or more emulsifiers which have different HLB values above and below the desired value. By employing the two emulsifiers together in appropriate ratio, it is readily feasible to attain a weighted average HLB value that promotes the formation of an emulsion.

Many suitable emulsifiers of high HLB are nonionic ester or ether emulsifiers comprising a polyoxyalkylene moiety, especially a polyoxyethylene moiety, often containing from about 2 to 80, and especially 5 to 60 oxyethylene units, and/or contain a polyhydroxy compound such as glycerol or sorbitol or other alditol as hydrophilic moiety. The hydrophilic moiety can contain polyoxypropylene. The emulsifiers additionally contain a hydrophobic alkyl, alkenyl or aralkyl moiety, normally containing from about 8 to 50 carbons and particularly from 10 to 30 carbons. The hydrophobic moiety can be either linear or branched and is often saturated, though it can be unsaturated, and is optionally fluorinated. The hydrophobic moiety can comprise a mixture of chain lengths, for example those deriving from tallow, lard, palm oil, sunflower seed oil or soya bean oil. Such nonionic surfactants can also be derived from a polyhydroxy compound such as glycerol or sorbitol or other alditols. Examples of emulsifiers include ceteareth-10 to -25, ceteth-10-25, steareth-10-25 (i.e. $C_{16}$ to $C_{18}$ alcohols ethoxylated with 10 to 25 ethylene oxide residues) and PEG-15-25 stearate or distearate. Other suitable examples include $C_{10}$-$C_{20}$ fatty acid mono, di or tri-glycerides. Further examples include $C_{18}$-$C_{22}$ fatty alcohol ethers of polyethylene oxides (8 to 12 EO).

Examples of emulsifiers, which typically have a low HLB value, often a value from 2 to 6 are fatty acid mono or possibly diesters of polyhydric alcohols such as glycerol, sorbitol, erythritol or trimethylolpropane. The fatty acyl moiety is often from $C_{14}$ to $C_{22}$ and is saturated in many instances, including cetyl, stearyl, arachidyl and behenyl. Examples include monoglycerides of palmitic or stearic acid, sorbitol mono or diesters of myristic, palmitic or stearic acid, and trimethylolpropane monoesters of stearic acid.

A particularly desirable class of emulsifiers comprises dimethicone copolymers, namely polyoxyalkylene modified dimethylpolysiloxanes. The polyoxyalkylene group is often a polyoxyethylene (POE) or polyoxypropylene (POP) or a copolymer of POE and POP. The copolymers often terminate in $C_1$ to $C_{12}$ alkyl groups.

Suitable emulsifiers and co-emulsifiers are widely available under many trade names and designations including Abil™, Arlace™, Brij™, Cremophor™, Dehydrol™, Dehymuls™, Emerest™, Lameform™, Pluronic™, Prisorine™, Quest PGPH™, Span™, Tween™, SF1228™, DC3225™ and Q2-5200™.

Optional Ingredients

Optionally, the subject composition may further comprise one or more deodorant actives. Suitable deodorant actives can comprise deodorant effective concentrations of deoperfumes, and/or microbicides, including particularly bactericides, such as, for example, chlorinated aromatics, including biguanide derivatives, of which materials known as Irgasan DP300™ (triclosan), Tricloban™, and chlorhexidine warrant specific mention. Another class comprises biguanide salts such as are available under the trade mark Cosmocil™. When present, many of the deodorant actives, including, for example microbicides, are commonly employed at a concentration of up to 2% by weight, more particularly up to 0.5% by weight, based on the total weight of the composition, with higher concentrations, being possible, as herein elsewhere noted, for deoperfumes.

Other optional ingredients include wash-off agents, often present in an amount of up to 10% by weight of the composition to assist in the removal of the formulation from skin or clothing. Such wash-off agents are typically nonionic surfactants such as esters or ethers containing a $C_8$ to $C_{22}$ alkyl moiety and a hydrophilic moiety which can comprise a polyoxyalkylene group (POE or POP) and/or a polyol.

Optionally, the formulation comprises one or more further gelling agents which can be employed in addition to the N-acyl amino acid gellant. Herein, the N-acyl amino acid gellant is the primary gelling agent, by which is meant that is employed at a concentration, by weight, that is higher than any further gelling agent. Desirably, the total amount of gelling agent inclusive of N-acyl amino acid gellant and further gelling agent does not exceed 30% by weight and preferably does not exceed 25% by weight of the oil phase The further gelling agents employable herein can be non-polymeric or polymeric. Included among such further gelling agents are amides of the formula:

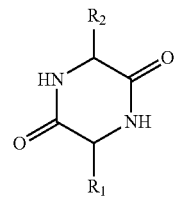

in which one of $R_1$ and $R_2$ represents an alkyl or alkyl ester group and the other represents an alkyl or alkaryl group. Examples of such amides are described in two papers by Habusa et al., entitled respectively *Cyclo(dipeptide)s as Low Molecular-Mass Gelling Agents to Harden Organic Fluids*, J. Chem. Soc. Commun., 1994, pp. 1401/2, and *Low Molecular Weight Gelators for Organic Fluids: Gelation Using a Family of Cyclo(dipeptide)s*, in the Journal of Colloid and Interface Science 224, 231-244 (2000), which description of amide structurants are incorporated herein by reference.

Other amides suitable for use herein as additional gelling agents are cyclodipeptides of the formula:

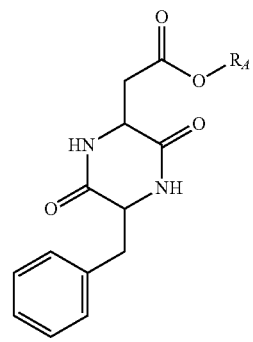

in which $R_A$ represents a carboxyclic or heterocylic group containing not more than 2 rings. Such materials are herein referred to as DOPA derivatives.

In DOPA derivatives, $R_A$ can comprise two fused rings, but preferably comprises a single six membered ring, either carbocylic or heterocyclic, or a ridged ring. When A is carbocyclic, it can be either saturated or unsaturated, preferably unsaturated or aromatic. When $R_A$ is heterocyclic, it is preferably saturated. Such DOPA derivatives are set forth in greater detail in US 2004/0223994, incorporated herein by reference. Desirable examples of $R_A$ include the residues from 4-alkyl phenol, such as 4-nonyl-phenol and 2,6-dialkyl- or 2,2,6,6-tetraalkyl-4-piperidinol, such as 2,2,6,6-tetramethyl-4-piperidinol.

Solid linear fatty alcohol and other wax may be included but are not preferred, and the total amount thereof should not exceed 2% by weight of the total composition, and preferably should not exceed 1% by weight of the total composition. In one or more embodiments the subject compositions are free of wax. Such further gelling agents exclude fatty acids or salts thereof, such as stearic acid or sodium stearate or 12-hydroxy stearic acid, because they can form insoluble precipitates with aluminum ions.

Polymeric gelling agents which can be employed can comprise organopolysiloxane elastomers such as reaction products of a vinyl terminated polysiloxane and a cross linking agent or alkyl or alkyl polyoxyalkylene-terminated poly (methyl substituted) or poly (phenyl substituted) siloxanes. A number of polyamides have also been disclosed as gelling agents for hydrophobic liquids. Polymers containing both siloxane and hydrogen bonding groups, which might be used as secondary gelling agents, have been disclosed in WO 97/36572 and WO 99/06473. Polyacrylamides, polyacrylates or polyalkylene oxides may also be used to structure or thicken the disperse phase.

In one or more embodiments, N-acyl amino acid amides comprises at least 90% by weight, preferably at least 95% by weight, of all gelling agent present in the composition.

The compositions herein can incorporate one or more cosmetic adjuncts conventionally used for antiperspirant emulsion sticks. Such cosmetic adjuncts can include skin feel improvers, such as talc or finely divided polyethylene, for example in an amount of up to about 1%; skin benefit agents such as allantoin or lipids, for example in an amount of up to 5%; colours; skin cooling agents other than the already mentioned alcohols, such a menthol and menthol derivatives, often in an amount of up to 2%, all of these percentages being by weight of the composition.

The subject composition may also comprise a minor amount of volatile oil, however, for the reasons described above, exclusive of perfume oil, it is generally desirable to minimize the amount of volatile oil present. Desirably, the amount of volatile oil (exclusive of perfume oil), if present, should not exceed 0.5 wt. % of the emulsion composition. Preferably the amount of volatile oil (exclusive of perfume oil), if present, does not exceed 0.3 wt. % of the emulsion composition and more preferably does not exceed 0.1 wt. % of the antiperspirant composition. Of particular interest in one or more embodiments are emulsion compositions that are free of volatile silicone oil.

A commonly employed adjunct is perfume. Perfume may include volatile and non-volatile oil and may be present as free and/or encapsulated fragrance. For purposes of this invention, unless otherwise indicated, perfume oil is considered as a separate component, and the amount thereof is not included as part of the "volatile" oil that is otherwise permitted in this subject compositions. The total amount of perfume (inclusive of all material present as part of fragrance encapsulate) is often from 0.001 to 5 wt %, more particularly from 0.01 to 4 wt. % and, even more particularly, from 0.1 to 3 wt. %, based on the total weight of the composition. Encapsulated fragrance may be formulated as shear sensitive or diffusive materials. These may be included in the oil phase, aqueous phase or in a combination of both.

Composition Preparation

Methods for preparing antiperspirant emulsion compositions are provided. Although letters or numbers may be associated with particular method steps in the description and claims, it should be understood that the such steps do not necessarily need to be performed in the order listed or in accordance with their associated designations. Additionally, although listed individually, some steps may be performed simultaneously. Alternatively, the steps may be carried out sequentially. It is also contemplated that steps may be combined.

A convenient process sequence for preparing a composition according to the present invention comprises forming a solution of the amido gelator with the liquid fatty alcohol and high and low RI emollient oils. This is normally carried out by agitating the mixture at a temperature sufficiently high that all the amido gelator dissolves (the dissolution temperature) such as a temperature in a range from 70 to 140° C. Other oil-soluble/miscible ingredients can be introduced into water-immiscible or oil phase, either before, with, or after the introduction of the amido gelator, as appropriate. Commonly, the resultant gelator solution is allowed to cool to a temperature that is intermediate between that at which the gelator dissolved and the temperature at which it would set, often reaching a temperature in the region of 60 to 110° C., with temperatures at the higher end of such range, for example, 95 to 110° C., being typical of processes in which shear is employed.

In some convenient preparative routes, it is desirable to dissolve all or a fraction of the amide-substituted gelator in the liquid fatty alcohol component of the composition, e.g., isostearyl alcohol or octyldodecanol. This enables the remainder of the oil phase fluids to avoid being heated to the temperature at which the gelators dissolve or melt.

Separately, the aqueous or hydrophilic phase is prepared by introduction of the antiperspirant active and other water soluble components into the liquid part of that phase (if this is necessary: antiperspirant actives can sometime be supplied in aqueous solution which can be utilized as is).

The emulsifier can be mixed into either the water-immiscible or the aqueous phase before they are mixed. When the emulsifier is a silicone containing surfactant, it is preferably added to the water-immiscible phase.

At the time they are combined, both the aqueous and water-immiscible phases are at elevated temperature without exceeding their respective boiling points. The temperature of the water-immiscible phase should be sufficiently high that the gelator is maintained in solution, but not so high that, when combined with the aqueous phase, the temperature of the combined phases exceeds the boiling point of the aqueous phase. Similarly, the temperature of the aqueous phase should not be so low that when combined with the water-immiscible phase, premature gelation occurs. In one or more embodiments, the aqueous and water immiscible phases are within 60° C., more particularly within 50° C., of each other just prior to their being combined.

If it is necessary to work at a temperature above the standard boiling temperature of the disperse, i.e., aqueous, phase or at a temperature where evaporation from this phase is significant, a pressurized apparatus can be used to allow a higher temperature to be reached. With the subject gelators this is usually unnecessary.

Temperature sensitive ingredients can be introduced to the resulting mixture when the mixture is at temperature that allows for the addition thereof without such ingredients being degraded. The mixture is then filled into dispensing containers, typically at temperature 5 to 40° C. above the regular setting temperature of the composition, and cooled or allowed to cool to ambient temperature. If desired, cooling may be assisted by blowing ambient or even refrigerated air over the containers and their contents.

To provide for appropriate RI matching, the RI of the prepared aqueous phase, inclusive of antiperspirant active, is typically measured, and the refractive index of the oil phase matched thereto. Typically RI matching of the oil phase to the aqueous phase is achieved by adjusting the content of the high and/or low RI oils.

Adjustment of the oil phase can be carried out prior to the addition of the gelator or subsequent to gelator addition, after the initial preparation of the continuous phase, since the gelator tends to have very little effect on the RI of the oil phase. However, knowing the individual RIs of the raw materials that make up the aqueous the oil phase, it is possible to calculate the amounts and relative amounts thereof that will provide a matching RI and, in the first instance, to prepare the oil phase to such formulation.

RI matching is typically carried out by measuring the RI of each separate component of the oil (continuous) phase (e.g., high and low RI oils, fatty alcohol, emulsifier (when present) and fragrance (when present)) as well as the RI of the total disperse (aqueous phase). All such RI measurements are carried out at 25° C. The total oil phase formulation is then calculated to match the RI of the aqueous phase using a weighted volume fraction method:

$$RI_{total} = \Sigma(RI * \text{vol fraction})_{a,b,c} \ldots$$

By keeping the concentration of certain oil phase components (e.g., fatty alcohol, emulsifier and fragrance) fixed, the ratio of high to low RI oils can be altered to conveniently match the RI of the oil phase to the aqueous phase. The oil phase components, exclusive of fragrance which, where used, is typically added to the finished emulsion at a temperature that avoids the volatilization thereof, ordinarily just prior to pouring into a suitable gel pack, are mixed to the calculated RI and employed in a production process as herein described.

The subject compositions are amenable to production by batch and continuous (including semi-continuous) processes. In a continuous process, the oil and aqueous phases can be made as described above and held with gentle agitation in separate vessels. Depending upon the scale of the process and the length of the heating/cooling/holding times, it may be desirable to add some thermally sensitive materials, for example, certain emulsifiers, to the oil phase after the cooling step. The oil phase may be held at any suitable temperature, typically within the range 120-97° C. The aqueous phase temperature should be adjusted such that when the two phases are combined in the correct ratio the temperature of the mixture is sufficiently high to avoid premature gelling. Typically, this will be in excess of 85° C.

The two phases (streams) can then be combined in the correct ratio at any point upstream of (or in) a device capable of providing intensive mixing (the primary intensive mixing device) such that the desired emulsion can be formed e.g. a Sonolator.

The combined streams can then be pumped through the primary intensive mixing device under the required conditions to form the desired emulsion while ensuring that the temperature of the mixture exceeds the gelation temperature. The emulsion formed in this manner may be packed directly into stick packs or sent to a holding vessel where the emulsion droplet size can be maintained or adjusted, by use of a second intensive mixing device (of similar or different design to the primary intensive mixing device) situated either inside the vessel or in a recirculation loop around the vessel, prior to packing the emulsion by filling into stick packs. If desired fragrance may be added to the mixture (emulsion) either as a third stream upstream or downstream of (or in) the primary intensive mixing device or directly into the holding vessel if used.

It is also possible to divide the oil phase formulation into two (or more) streams as desired. This allows the temperatures to which specific formulation components are exposed to be more closely controlled and may be desirable for thermally sensitive components, such as, for example, certain emulsifiers. Several streams may then be combined in the correct ratio upstream of or indeed downstream of the primary mixing device depending on the function of the formulation component and provided that the temperature of the combined system exceeds the gelation temperature. The process may then continue as described above.

In another embodiment of this invention there is provided a method of producing a water-in oil antiperspirant emulsion composition which comprises the steps of:

A) producing an aqueous phase of a target refractive index (RI) by solubilizing antiperspirant active in hydrophilic carrier comprising water;
B) providing an oil phase comprising: at least one amido gelator, at least one fatty alcohol that is liquid at 25° C., at least one primary emollient oil having an RI that is at least 0.005 units, preferably at least 0.01 units, above the target RI of the aqueous phase, and at least one secondary emollient oil having an RI that is at least 0.005 units, preferably at least 0.01 units below the target RI of the aqueous phase;
C) dissolving emulsifier in the oil and/or aqueous phase;
D) measuring the RI of the aqueous phase;
E) adjusting level of primary and/or secondary emollient oil in the oil phase to form an adjusted oil phase having an RI that is within 0.005 units, preferably within 0.002 units, of the measured RI of the aqueous phase;
F) combining the aqueous phase and the adjusted oil phase under conditions of shear sufficient to form an emulsion composition;
G) filling stick dispensers with the emulsion composition; and
H) allowing the emulsion composition to solidify in the filled dispensers, wherein:
   (a) the composition contains from 0 to 0.5 wt. %, preferably from 0 to 0.1 wt. % of volatile solvent, exclusive of perfume oil;
   (b) the solidified composition is at least translucent;
   (c) the primary and secondary oils account for from 5 to 65% by weigh of the adjusted oil phase;
   (d) in the adjusted oil phase, the ratio, by weight, of the combination of primary non-volatile emollient oil and secondary non-volatile emollient oil to fatty alcohol is from 2:1 to 1:20; and
   (e) in the adjusted oil phase, the ratio, by weight, of primary non-volatile emollient oil to secondary non-volatile emollient oil is from 1:20 to 20:1.

Preferably the emulsifier comprises polyoxyalkylene modified dimethylpolysiloxane, the polyoxyalkylene modified dimethylpolysiloxane being preferably dissolved in the oil phase.

Product Dispenser

Emulsion sticks according to the present invention are normally housed in dispensing containers, the shape and size of which, the materials of their construction and the mechanisms employed therein for dispensing antiperspirant stick compositions. Thus, by way of example, an antiperspirant stick is often housed in a barrel, commonly of circular or elliptical transverse cross section, having an open end through which the stick can pass and an opposed closed end, commonly comprising a platform or elevator that is axially moveable along the barrel. The platform can be raised by the insertion of a finger or more commonly by rotation of an externally exposed rotor wheel that rotates a threaded spindle extending axially through a cooperating threaded bore in the platform. The barrel normally also has a removable cap that can fit over its open end. The barrel is normally made from an extrudable thermoplastic such as, for example, polypropylene or polyethylene.

EXAMPLES

The following non-limiting examples are provided to further illustrate the invention; the invention is not limited thereto.

As reported in the Examples % Light Transmission and Hardness Values were obtained following the following procedures.

Clarity of Formulation—% Light Transmission

Translucency of a composition measured by placing a sample of standardized thickness in the light path of a spectrophotometer and measuring transmittance, as a percentage of light transmitted in the absence of the gel.

This test is carried out using a dual-beam Perkin Elmer Lambda 40 spectrophotometer. The sample of composition is poured hot into a 4.5 ml cuvette made of poly(methylmethacrylate) (PMMA) and allowed to cool to an ambient temperature of 20-25° C. and solidify. Such a cuvette gives a 1 cm thickness of composition. Measurement is carried out at 580 nm, with an identical but empty cuvette in the reference beam of the spectrophotometer, after the sample in the cuvette has been held for 24 hours. Transmittance is measured on the gelled composition at 25° C. Throughout the specification and claims, % Light Transmission refers to the clarity of a composition as measured by this procedure.

Hardness: Penetrometer Protocol

The hardness of a stick composition is herein which determined by penetrometry testing that measures the resistance of the stick to a penetrometer probe. The procedure utilizes a lab plant PNT penetrometer equipped with a Seta wax needle (weight 2.5 grams) having a cone angle at the point of the needle of 9°10"+/−15". Penetration hardness measurements are obtained on a sample of the composition with a flat upper surface. The needle is lowered onto the upper surface of the composition and then a penetration measurement is conducted by allowing the needle with its holder to drop under a total weight, (i.e. the combined weight of needle and holder) of 50 grams for a period of five seconds after which the depth of penetration is noted. The test is carried out at a number of points on each sample and the results are averaged.

Measurements on the stick are performed in the stick barrel. The stick is wound up to project from the open end of the barrel, and then cut off to leave a flat, uniform upper surface onto which the needle is lowered as described above. Penetration measurements are taken at six different points on said upper surface of stick surface as described above. Hardness values are reported as the average value of the 6 measurements.

Utilizing a test of this nature, an appropriate hardness for use in an open-ended dispensing container is a penetration of less than 30 mm in this test, for example in a range from 2 to 30 mm. Preferably the penetration is in a range from 5 mm to 20 mm, with penetration values to of 8 to 15 being of particular interest. The following constituents were employed in exemplified and comparison emulsion sticks hereinafter.

TABLE 1

| Refractive Index | |
| --- | --- |
| Raw Material | Refractive Index |
| Oil 1 - DC245 (Cyclopentylsiloxane aka D5)*** | 1.39602 |
| Oil 2 - Cetiol OE (Dioctyl ether)* | 1.43103 |
| Oil 3 - Cetiol CC (Dioctyl carbonate)* | 1.43428 |
| Oil 4 - Crodamol IPP-LQ-(GD)** (isopropyl palmitate) | 1.43642 |

TABLE 1-continued

| Refractive Index | |
| --- | --- |
| Raw Material | Refractive Index |
| Oil 5 - Crodamol IPM-LQ-(GD)** (isopropyl myristate) | 1.43266 |
| Oil 6 - Xiameter PMX-200 - 350cs*** (Dimethicone) | 1.40333 |
| Oil 7 - DC200 - 5000cs*** (Dimethicone) | 1.40364 |
| Oil 8 - Crodamol GTEH-LQ(MV)** (Triethylhexanoin) | 1.44405 |
| Finsolv TN**** ($C_{12-15}$ alkyl benzoate) | 1.4841 |
| Fluid AP***** (PPG14-butyl ether) | 1.4465 |
| Prisorine 3515** (Isostearyl alcohol) | 1.4559 |

*From BASF
**From Croda
***From Dow Corning
****From Finetex
*****From Amerchol

Oil phases were made according to the formulations described in Table 2 by direct weighing of the components into 120 ml glass jars with gentle mixing.

TABLE 2

| Oil phase formulations | | | | | |
| --- | --- | --- | --- | --- | --- |
| Raw Material | Oil Phase Composition | | | | |
| Wt. (g) | OP 1 | OP 2 | OP3 | OP 4 | OP5 |
| Abil EM90 (PEG/PPG-10/1 Dimethicone)* | 1.21 | 1.22 | 1.20 | 1.21 | 1.21 |
| Finsolv TN | 22.73 | 20.40 | 20.02 | 19.76 | 20.21 |
| Prisorine 3515 | 27.36 | 27.38 | 27.36 | 27.35 | 27.36 |
| Oil 1 (D5) | 3.50 | 0.00 | 0.00 | 0.00 | 0.00 |
| Oil 2 | 0.00 | 5.81 | 0.00 | 0.00 | 0.00 |
| Oil 3 | 0.00 | 0.00 | 6.20 | 0.00 | 0.00 |
| Oil 4 | 0.00 | 0.00 | 0.00 | 6.48 | 0.00 |
| Oil 5 | 0.00 | 0.00 | 0.00 | 0.00 | 6.00 |

*From Degussa

Jars containing the oil phase formulations were then opened and placed in a lab oven at;

50° C. for 5 hours

85° C. for 5.5 hours

85° C. for 6 hours

At the end of each storage condition the jars containing the oil phase mixtures were tightly closed and allowed to cool to 25° C. and the refractive index was measured. The samples were sequentially exposed to each storage condition in the order indicated. The refractive index (RI) values obtained for the various oil phase mixtures are reported in Table 3. Owing to the volatility of cyclopentasiloxane, the oil phase in which cyclopentasiloxane was replaced by non-volatile oil had RI values that were generally more stable in this open system testing than that of oil phase containing cyclopentasiloxane. That is to say, the oil phase mixtures in which cyclopentasiloxane was replaced with a non-volatile oil were more stable to RI change, when heated in an open vessel, than the cyclopentasiloxane containing control.

TABLE 3

Oil Phase Refractive Indices

| Time and Temp | OP1 RI Measured | OP1 Difference | OP2 RI Measured | OP2 Difference | OP3 Difference | OP3 Difference |
|---|---|---|---|---|---|---|
| Initial | 1.46191 | 0.000000 | 1.46121 | 0.000000 | 0.000000 | 0.000000 |
| 5.0 hrs @ 50° C. | 1.46197 | −0.000060 | 1.46121 | 0.000000 | 0.000010 | 0.000010 |
| 5.5 hrs @ 85° C. | 1.46237 | −0.000460 | 1.46149 | −0.000280 | −0.000250 | −0.000270 |
| 6.0 hrs @ 85° C. | 1.46277 | −0.000860 | 1.46167 | −0.000460 | −0.000420 | −0.000400 |

| Time and Temp | OP4 Difference | OP4 Difference | OP5 RI Measured | OP5 Difference |
|---|---|---|---|---|
| Initial | 0.000000 | 0.000000 | 1.46132 | 0.000000 |
| 5.0 hrs @ 50° C. | 0.000010 | 0.000010 | 1.46131 | 0.000010 |
| 5.5 hrs @ 85° C. | −0.000250 | −0.000270 | 1.46161 | −0.000290 |
| 6.0 hrs @ 85° C. | −0.000420 | −0.000400 | 1.46173 | −0.000410 |

Full emulsion sticks according to the formulation described in Table 4 were prepared from separate aqueous and oil phases made by the following general procedures.

Aqueous Phase

Weigh water into vessel;

start stirring;

slowly add antiperspirant active;

allow the active to dissolve;

add glycine;

continue mixing until all solids are fully dissolved; applying heat as needed to speed up the process of dissolution.

Oil Phase

Weigh liquid fatty alcohol and high and low RI oils into vessel;

start mixing;

slowly add amido gelator;

heat mixture with constant stirring to ca. 120° C. and hold until dissolution of the solids is complete; and allow to cool to between 99 and 97° C. with gentle mixing.

The aqueous phase was prepared first and the RI measured at 25° C., to allow the oil phase formulation to be modified as required, by adjusting the ratios of the high and low RI oils, to achieve RI matching to the aqueous phase. The aqueous phase refractive indices (RI) were 1.45809 for Examples A to E; and 1.45701 for Examples F to I.

To prepare the final formulation, the aqueous phase was heated to 75° C. in a sealed jar and was then added, steadily, to the vessel containing the oil phase, which had been allowed to cool to 99-97° C. Mixing of the oil phase was provided by a dip-in Silverson L4RT mixer fitted with a 22 mm diameter mixing head fitted with a disperser screen. Mixing intensity was increased during addition of the aqueous phase by increasing the speed of the mixer from 1000 rpm to 7500 rpm. The temperature of the combined phase typically fell to 90-85° C. after addition of the aqueous phase. The combined phases were allowed to mix for a further 5 minutes at 90-85° C. and 7500 rpm to allow the desired emulsion to be formed. The % Light Transmission of the liquid full formulation emulsion compositions was measured following the procedure described above. The emulsion compositions were allowed to solidify and hardness values were obtained for the solidified sticks following the procedure described above. % Light Transmission and Hardness values are reported in Table 4.

TABLE 4

Emulsion Stick Compositions

| Raw Materials | A (comp) Batch 1 wt % | B Batch 1 wt % | C Batch 1 wt % | D Batch 1 wt % | E Batch 1 wt % |
|---|---|---|---|---|---|
| GP1* | 4.00 | 4.00 | 4.00 | 4.00 | 4.00 |
| GA01** | 4.00 | 4.00 | 4.00 | 4.00 | 4.00 |
| Abil EM90 | 1.20 | 1.20 | 1.20 | 1.20 | 1.20 |
| FinsolvTN | 20.07 | 16.59 | 15.91 | 15.41 | 16.26 |
| Prisorine 3515 | 27.35 | 27.35 | 27.35 | 27.35 | 27.35 |
| Oil 1 | 6.13 | 0.00 | 0.00 | 0.00 | 0.00 |
| Oil 2 | 0.00 | 9.61 | 0.00 | 0.00 | 0.00 |
| Oil 3 | 0.00 | 0.00 | 10.29 | 0.00 | 0.00 |
| Oil 4 | 0.00 | 0.00 | 0.00 | 10.79 | 0.00 |
| Oil 5 | 0.00 | 0.00 | 0.00 | 0.00 | 9.94 |
| Oil 6 | 0.00 | 0.00 | 0.00 | 0.00 | 0.00 |
| Oil 7 | 0.00 | 0.00 | 0.00 | 0.00 | 0.00 |
| Oil 8 | 0.00 | 0.00 | 0.00 | 0.00 | 0.00 |
| Aluminum Zirconium Tetrachlorohydrex Gly | 19.00 | 19.00 | 19.00 | 19.00 | 19.00 |
| Water | 12.66 | 12.66 | 12.66 | 12.66 | 12.66 |
| Glycine | 5.59 | 5.59 | 5.59 | 5.59 | 5.59 |
| Total | 100.00 | 100.00 | 100.00 | 100.00 | 100.00 |
| % Light Transmission (580 nm) | 16.97 | 21.48 | 24.95 | 27.66 | 21.07 |
| Hardness (mm) | 10.02 | 9.77 | 9.36 | 9.36 | 9.73 |

It is clear from the results in table 4 that the comparative example 'A' had a much lower % light transmission value than examples B to E, all according to the invention, which displayed improved clarity as shown by the % light transmission values. All of the sticks had good hardness.

TABLE 5

Emulsion Stick Compositions

| Raw Materials | F (comp) Batch 2 wt % | G (comp) Batch 2 wt % | H (comp) Batch 2 wt % | I Batch 2 Wt/% |
|---|---|---|---|---|
| GP1* | 4.00 | 4.00 | 4.00 | 4..00 |
| GA01** | 4.00 | 4.00 | 4.00 | 4.00 |
| Abil EM90 | 1.20 | 1.20 | 1.20 | 1.20 |
| FinsolvTN | 19.33 | 18.65 | 18.62 | 11.54 |
| Prisorine 3515 | 27.35 | 27.35 | 27.35 | 27.35 |
| Oil 1 | 6.87 | 0.00 | 0.00 | 0.00 |
| Oil 2 | 0.00 | 0.00 | 0.00 | 0.00 |
| Oil 3 | 0.00 | 0.00 | 0.00 | 0.00 |
| Oil 4 | 0.00 | 0.00 | 0.00 | 0.00 |

TABLE 5-continued

Emulsion Stick Compositions

| Raw Materials | F (comp) Batch 2 wt % | G (comp) Batch 2 wt % | H (comp) Batch 2 wt % | I Batch 2 Wt/% |
|---|---|---|---|---|
| Oil 5 | 0.00 | 0.00 | 0.00 | 0.00 |
| Oil 6 | 0.00 | 7.55 | 0.00 | 0.00 |
| Oil 7 | 0.00 | 0.00 | 7.58 | 0.00 |
| Oil 8 | 0.00 | 0.00 | 0.00 | 14.66 |
| Aluminum Zirconium Tetrachlorohydrex Gly | 19.00 | 19.00 | 19.00 | 19.00 |
| Water | 12.66 | 12.66 | 12.66 | 12.66 |
| Glycine | 5.59 | 5.59 | 5.59 | 5.59 |
| Total | 100.00 | 100.00 | 100.00 | 100.00 |
| % Light Transmission (580 nm) | 22.20 | Oil not miscible | | 20.26 |
| Hardness (mm) | 10.45 | 9.96 | 9.99 | 10.01 |

*N-lauryl-L-glutamic acid, di-n-butylamide from Ajinomoto.
**N-ethylhexanoyl-L-glutamic acid, di-n-butylamide from Ajinomoto.

A second batch of examples was made. Note that examples from different batches may have different properties from an earlier batch, therefore the most valid comparisons are comparisons internally between samples from the same batch, not comparisons between batch 1 and 2.

In batch 2, all of the sticks had good hardness. Owing to miscibility issues between the dimethicone oils and the rest of the oil phase, emulsion sticks G and H, lacked clarity. Example I is according to the invention, but is not preferred, and was found to be no better (indeed slightly worse) than the comparative example F in terms of clarity as measured by % light transmittance.

Evaluation of the compositions by a trained test panel indicated that emulsion sticks prepared with oils 2 to 5 and 8 (i.e. compositions B to F, and I) were, from a tactile sensory perspective, generally comparable (not noticeably different) to the comparative emulsion stick prepared using cyclopentasiloxane (i.e. emulsion stick A).

The invention claimed is:

1. A water-in-oil emulsion antiperspirant composition comprising:
   A) an aqueous phase containing dissolved antiperspirant active
   B) an oil phase comprising:
      i) at least one amido gelator;
      ii) at least one fatty alcohol that is liquid at 25° C., the fatty alcohol comprising isostearyl alcohol;
      iii) at least one primary non-volatile emollient oil having a refractive index (RI) that is from 1.47 to 1.56, wherein the primary non-volatile emollient oil comprises $C_{12}$ to $C_{15}$ alkyl benzoate;
      iv) at least one secondary non-volatile emollient oil having an RI that is from 1.38 to 1.45, the secondary non-volatile emollient oil comprising at least one of the following: dioctyl ether, dioctyl carbonate, isopropyl palmitate, isopropyl myristate, PPG-14 butyl ether, or triethylhexanoin; and
   C) an emulsifier,
   wherein:
      a) the composition is in the form of a solid stick that is at least translucent in appearance; and
      b) the primary and secondary emollient oils combined account for from 5 to 65% by weight the oil phase;
      c) the composition contains from 0 to 0.5 wt. % of volatile oil, exclusive of perfume oil;
      d) the ratio, by weight, of the combination of primary non-volatile, emollient oil and secondary non-volatile emollient oil to fatty alcohol is from 2:1 to 1:20;
      e) the ratio, by weight of primary non-volatile emollient oil to secondary non-volatile emollient oil is from 1:20 to 20:1;
      f) the ratio, by weight, of fatty alcohol to amido gelator is from 2:1 to 6:1; and,
      g) if present, the composition contains at most 2.5 wt. % of non-volatile aliphatic dimethicone oil.

2. The composition according to claim 1 having a % Light Transmission Value greater than 5%.

3. The composition according to claim 1, wherein the amido gelator comprises at least one N-acyl amino acid amide.

4. The composition according to claim 1, which is free of volatile silicone oil.

5. The composition according to claim 1, which further comprises perfume oil and/or glycine.

6. The composition according to claim 1, wherein the amido gelator comprises N-lauryl-L-glutamic acid, di-n-butyl amide and N-ethyl hexanoyl-L-glutamic acid, di-n-butylamide.

7. The composition according to claim 1, wherein the RI of the aqueous and oil phases are matched to within 0.002 units.

8. The composition according to claim 1, wherein the composition comprises from 4 to 12% by weight, based on the total weight thereof, of a combination of amido gelators of the formula $A^x$—CO—$R^x$ and $A^y$—CO—$R^y$ wherein $R^x$ represents a branched alkyl group containing from 4 to 12 carbon atoms, $R^Y$ represents a linear alkyl group containing from 9 to 21 carbon atoms and $A^x$ and $A^Y$ independently represent an amino acid amide residue:

$$-\underset{H}{N}\diagup\overset{(CH_2)_n-CONH-R^z}{\diagdown CONH-R^z}$$

in which n represents an integer of 1 or 2 and $R^Z$ represents an alkyl group, which can be linear or branched, containing from 1 to 10 carbon atoms, which $R^Z$ groups can be the same or different.

9. The composition according to claim 1, wherein the emulsifier comprises polyoxyalkylene modified dimethylpolysiloxane.

10. The composition according to claim 1, wherein the amido gelator comprises at least 90% by weight of all gelling agent present in the composition.

11. The composition according to claim 1, wherein the total amount of wax, if present, does not exceed 1% by weight, based on the total weight of the composition.

12. The composition according to claim 1, wherein the secondary non-volatile oil is selected from the group consisting of dioctyl ether, dioctyl carbonate, isopropyl palmitate, isopropyl myristate, PPG-14 butyl ether, or a mixture thereof.

13. A method of producing a water-in oil antiperspirant emulsion composition which comprises the steps of:
   A) producing an aqueous phase of a target refractive index (RI) by solubilizing antiperspirant active in hydrophilic carrier comprising water;
   B) providing an oil phase comprising: at least one amido gelator, at least one fatty alcohol that is liquid at 25° C., the fatty alcohol comprising isostearyl alcohol; at least one primary emollient oil having an RI that is from 1.47 to 1.56, wherein the primary non-volatile emollient oil comprises $C_{12}$ to $C_{15}$ alkyl benzoate; and at least one secondary emollient oil having an RI that is from 1.38 to 1.45 the secondary non-volatile emollient oil comprising at least one of the following: dioctyl ether, dioctyl carbonate, isopropyl palmitate, isopropyl myristate, PPG-14 butyl ether, or triethylhexanoin; and optionally non-volatile aliphatic dimethicone oil;

C) dissolving emulsifier in the oil and/or aqueous phase;

D) measuring the RI of the aqueous phase;

E) adjusting level of primary and/or secondary emollient oil in the oil phase to form an adjusted oil phase having an RI that is within 0.005 units of the measured RI of the aqueous phase;

F) combining the aqueous phase and the adjusted oil phase under conditions of shear sufficient to form an emulsion composition;

G) filling stick dispensers with the emulsion composition; and

H) allowing the emulsion composition to solidify in the filled dispensers, wherein:
 a) the emulsion composition contains from 0 to 0.5 wt. % of volatile solvent, exclusive of perfume oil;
 b) the solidified composition is at least translucent;
 c) the primary and secondary oils account for from 5 to 65% by weigh of the adjusted oil phase;
 d) in the adjusted oil phase, the ratio, by weight, of the combination of primary non-volatile emollient oil and secondary non-volatile emollient oil to fatty alcohol is from 2:1 to 1:20;
 e) in the adjusted oil phase, the ratio, by weight, of primary non-volatile emollient oil to secondary non-volatile emollient oil is from 1:20 to 20:1
 f) in the adjusted oil phase, the ratio, by weight, of fatty alcohol to amido gelator s from 2:1 to 6:1; and,
 g) if present, the composition contains at most 2.5 wt. % of non-volatile aliphatic dimethicone oil.

14. The method according to claim 13 wherein the emulsifier comprises polyoxyalkylene modified dimethylpolysiloxane.

* * * * *